US008342744B2

(12) United States Patent
Nishimura et al.

(10) Patent No.: US 8,342,744 B2
(45) Date of Patent: Jan. 1, 2013

(54) DIFFERENTIAL SCANNING CALORIMETER

(75) Inventors: Shinya Nishimura, Chiba (JP); Kentaro Yamada, Chiba (JP); Hirohito Fujiwara, Chiba (JP)

(73) Assignee: SII NanoTechnology Inc. (JP)

( * ) Notice: Subject to any disclaimer, the term of this patent is extended or adjusted under 35 U.S.C. 154(b) by 500 days.

(21) Appl. No.: 12/658,828

(22) Filed: Feb. 16, 2010

(65) Prior Publication Data

US 2010/0220764 A1 Sep. 2, 2010

(30) Foreign Application Priority Data

Feb. 20, 2009 (JP) ................................. 2009-037298

(51) Int. Cl.
*G01K 17/04* (2006.01)
*G01N 25/20* (2006.01)
(52) U.S. Cl. ............................... 374/11; 374/31; 374/29
(58) Field of Classification Search ............... 374/10–12, 374/29–39, 208, 100; 422/51; 436/147
See application file for complete search history.

(56) References Cited

U.S. PATENT DOCUMENTS

| | | | | |
|---|---|---|---|---|
| 5,484,204 A * | 1/1996 | Damley | ........................... | 374/10 |
| 7,275,862 B2 * | 10/2007 | Nishimura et al. | ............. | 374/11 |
| 7,802,916 B2 * | 9/2010 | Teramoto | ........................ | 374/11 |
| 8,066,429 B2 * | 11/2011 | Danley | ............................. | 374/31 |
| 8,087,821 B2 * | 1/2012 | Danley | ............................. | 374/12 |
| 2005/0053113 A1 * | 3/2005 | Clary et al. | ................... | 372/108 |

FOREIGN PATENT DOCUMENTS

| | | | | |
|---|---|---|---|---|
| JP | 05147928 | A | * | 6/1993 |
| JP | 06058047 | A | * | 3/1994 |
| JP | 08105852 | A | * | 4/1996 |

OTHER PUBLICATIONS

Patent Abstracts of Japan, publication No. 07-122619, publication date May 12, 1995.
Patent Abstracts of Japan, publication No. 2002-310965, publication date Oct. 23, 2002.
Patent Abstracts of Japan, publication No. 2006-058047, publication date Mar. 2, 2006.

* cited by examiner

*Primary Examiner* — Gail Verbitsky
(74) *Attorney, Agent, or Firm* — Adams & Wilks

(57) ABSTRACT

The differential scanning calorimeter includes: a heat sink, which stores a measuring sample and a reference material; a heater, which heats the heat sink; a cooling block, which is separated away from the heat sink, and positioned below the heat sink; a thermal resistor, which is connected between the heat sink and the cooling block, and forms a heat flow path therebetween; a cooling head, which is detachably fitted to the cooling block, and is cooled by an external cooling device; and differential heat flow detectors, which output a temperature difference between the measuring sample and the reference material as a heat-flow-difference signal, in which: the cooling block forms a side wall to fit the bore of the cooling head outward from the joint of the thermal resistance body; the top surface of the cooling head is lower than the joint.

3 Claims, 7 Drawing Sheets

F I G. 2
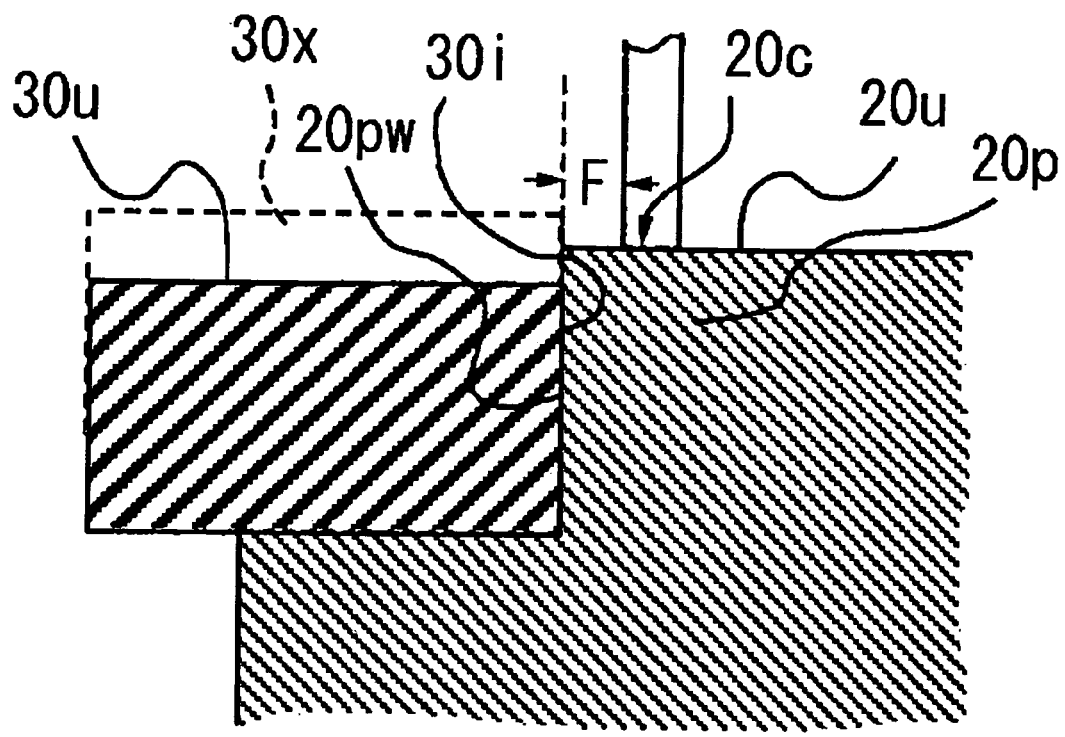

F I G . 4
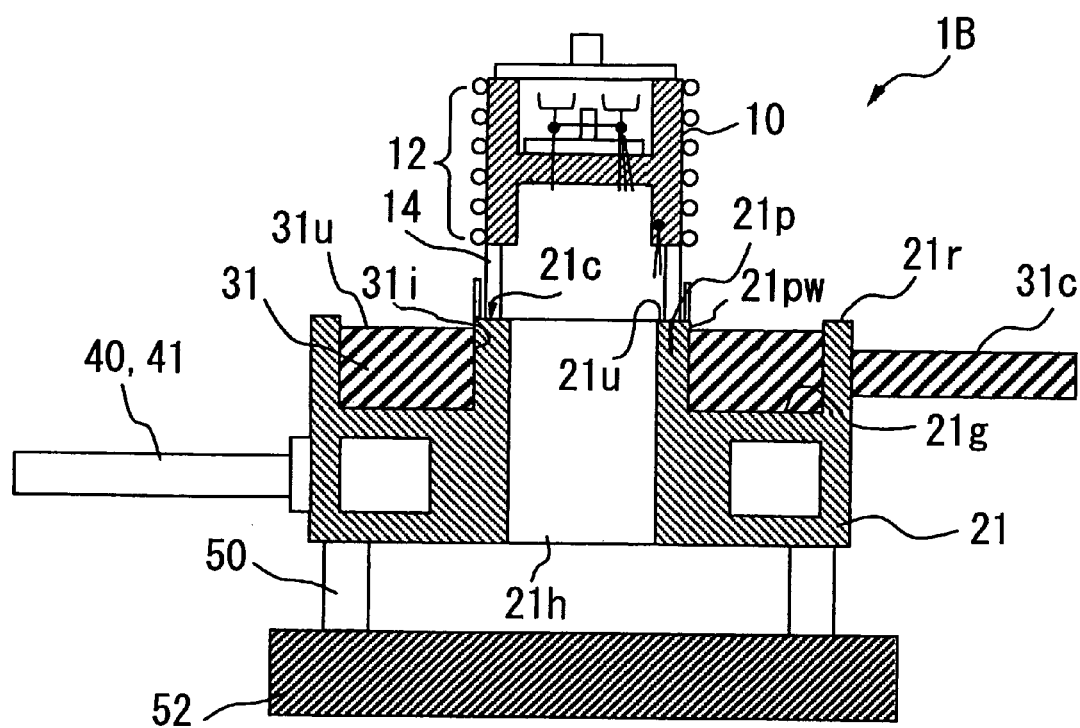

DIFFERENTIAL SCANNING CALORIMETER

BACKGROUND OF THE INVENTION

1. Field of the Invention

The present invention relates to a differential scanning calorimeter, to which a cooling head to be cooled by an external cooling device is detachably connected.

2. Description of the Related Art

The differential scanning calorimeter is a thermal analysis device which changes temperatures of a measuring sample and a reference material stored in a heat sink at a constant speed, to thereby measure a difference in heat flow flowing through the measuring sample and the reference material. The differential scanning calorimeter includes a heater for heating the heat sink and a cooling mechanism for cooling the heat sink. To the cooling mechanism, a gas cooling device (JP 07-122619 B) or an electric cooling device is connected from the outside, to thereby perform cooling. The gas cooling device uses gas obtained by vaporizing liquefied nitrogen or the like, and the electric cooling device uses a coolant cooled by a compressor.

Further, the following differential scanning calorimeter is disclosed as a thermal analysis device (JP 2006-58047 A): a differential scanning calorimeter in which a cooling mechanism itself has an insertion hole formed therein, into which a cooling head is inserted and which allows an external electric cooling device to be detachably connected to the cooling mechanism, and a discharge flow path continuous with the insertion hole is provided so as to enable gas cooling of the cooling mechanism itself.

Further, there is disclosed a scanning calorimeter in which a cooling flange provided with a cylindrical disk is connected through a thermal resistor to the lower portion of the heat sink (JP 2002-310965 A (FIG. 1 and paragraph 0045)).

However, the gas cooling device involves complicated supplement of the coolant and high running cost, while the electric cooling device is allowed to be used only in a limited temperature range. Therefore, when only one of the gas cooling device and the electric cooling device is allowed to be used for cooling, measurement by the differential scanning calorimeter is restricted.

Further, in the case of the technology described in JP 2002-310965 A, the external cooling device is mounted on a top surface 12 of a cooling flange (cooling block) 10. Therefore, the cooling head of the cooling device is adjacent to a thermal resistor 9 on the cooling flange 10 so as to directly face thereto, and unignorable heat inflow through an air layer occurs between the cooling head and the thermal resistor 9. This occurs because the cooling head and the thermal resistor 9 have a temperature difference of 100° C. or higher therebetween. In this case, thermal effects by radiation, convection, and the like occur between the cooling head and the thermal resistor 9, which leads to imbalance and destabilization of the heat conduction to the heat sink. Meanwhile, when the cooling head is separated away from the thermal resistor 9 to be brought into contact with the cooling flange 10, thermal resistance occurs in the cooling flange 10. As a result, temperature distribution of the cooling flange 10 becomes wider, and cooling efficiency is reduced.

On the other hand, in the case of the technology described in JP 2006-58047 A, the cooling head is completely housed in the cooling mechanism (cooling block), and hence the problem of heat inflow between the cooling head and the thermal resistor does not occur. However, the cylindrical cooling head is inserted into the cooling block at a deviated position, and hence there is a risk that the cooling block is not uniformly cooled. Regarding this risk, the technology described in JP 2006-58047 A has room for improvement.

SUMMARY OF THE INVENTION

The present invention has been made for solving the above-mentioned problems, and an object thereof is to provide a differential scanning calorimeter capable of suppressing heat inflow from the cooling head to the thermal resistor between the heat sink and the cooling block when the cooling head to be cooled by the external cooling device is connected to the cooling block, to thereby improve cooling speed, measurement accuracy, and cooling efficiency.

In order to achieve the above-mentioned object, according to the present invention, a differential scanning calorimeter includes: a heat sink, which stores a measuring sample and a reference material; a heater, which heats the heat sink; a cooling block, which is separated away from the heat sink, and is positioned below the heat sink; a thermal resistor, which is connected between the heat sink and the cooling block, and forms a heat flow path therebetween; a cooling head, which is provided with an inner hole for allowing the cooling head to be detachably fitted to the cooling block, and is cooled by an external cooling device; and differential heat flow detectors, which output a temperature difference between the measuring sample and the reference material as a heat-flow-difference signal, in which: the cooling block has a side wall, which is formed on an outside of a connected portion connected to the thermal resistor, and is fitted to the inner hole; and the cooling head is arranged so that an upper surface thereof is positioned flush with or below the connected portion.

The upper surface of the cooling head is positioned flush with or below the connected portion as described above, and hence the thermal resistor does not directly face the cooling head. Therefore, it is possible to suppress heat inflow through an air layer between the thermal resistor and the cooling head. Further, the side wall fitted into the inner hole of the cooling head is positioned on the outside of the connected portion, and hence a gap is inevitably formed between an inner surface of the cooling head and the connected portion in a side view. Therefore, it is possible to prevent direct contact between the inner surface of the cooling head and the thermal resistor. Further, heat conduction is performed through a fitting portion between the inner hole of the cooling head and the side wall. Therefore, compared with the heat conduction through another fitting portion (for example, fitting portion between a lower surface of the cooling head and an upper surface of the cooling block), the heat flow path to the thermal resistor may be reduced. As a result, cooling speed may be increased and cooling efficiency may be improved.

Further, the inner surface of the cooling head surrounds the side wall and comes in contact therewith. Therefore, heat conduction loss between the cooling head and the cooling block is small, and hence the cooling efficiency may be enhanced.

The side wall may include an outer peripheral surface of a protruding portion protruding upward or downward from the cooling block.

With this structure, it is sufficient that the protruding portion is fitted into the inner hole of the cooling head, thereby enabling secure fitting.

In one of an upper surface and a lower surface of the cooling block, an annular groove may be formed, the annular groove being sectioned by the protruding portion and an outer peripheral ring surrounding the protruding portion from an outside thereof with the annular groove therebetween, and the cooling head may be housed in the annular groove and the protruding portion may be fitted with the inner hole.

With this structure, the heat conduction is performed also through a contact portion between an outer periphery of the cooling head and an inner surface of the outer peripheral ring. Therefore, heat conduction loss between the cooling head and the cooling block is further reduced, thereby further enhancing cooling efficiency.

According to the present invention, it is possible to suppress heat inflow from the cooling head to the thermal resistor between the heat sink and the cooling block when the cooling head to be cooled by the external cooling device is connected to the cooling block, and to improve cooling speed, measurement accuracy, and cooling efficiency.

BRIEF DESCRIPTION OF THE DRAWINGS

In the accompanying drawings:

FIG. 2 is a partial enlarged view of a vicinity of a connected portion of a cooling block;

FIG. 4 is a sectional view illustrating a structure of a differential scanning calorimeter according to a second embodiment of the present invention;

DETAILED DESCRIPTION OF THE PREFERRED EMBODIMENTS

Hereinafter, embodiments of the present invention are described with reference to the drawings.

Figure 1:
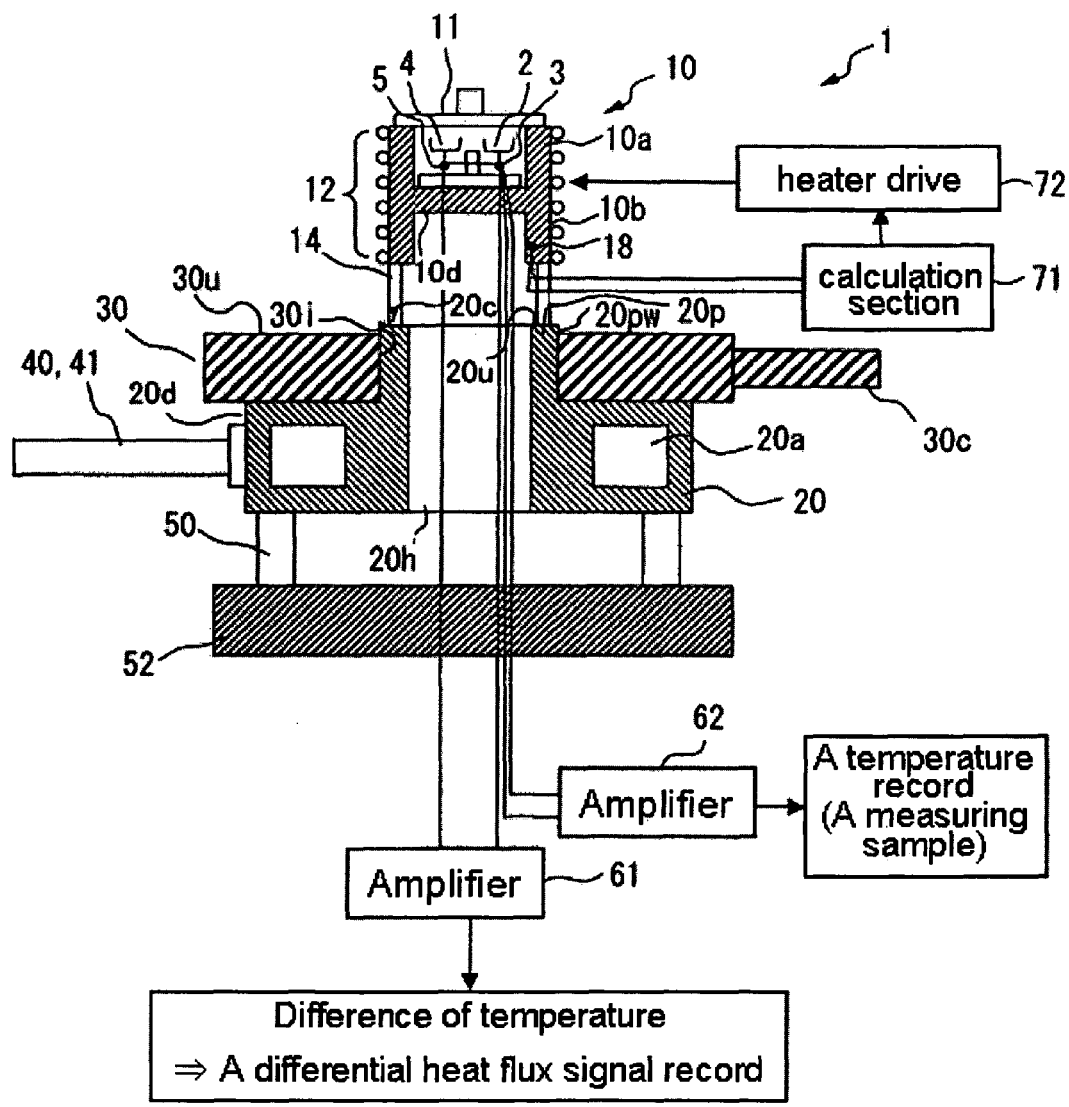
FIG. 1 is a sectional view illustrating a structure of a differential scanning calorimeter according to a first embodiment of the present invention.

FIG. 1 is a sectional view illustrating a structure of a differential scanning calorimeter 1 according to a first embodiment of the present invention. The differential scanning calorimeter 1 includes: a heat sink 10, which stores a measuring sample and a reference material; a coil-like heater 12, which is wound around the outer periphery of the heat sink 10 and heats the heat sink 10; a cooling block 20 arranged below the heat sink 10 while being separated away therefrom; a thermal resistor 14, which is connected between the heat sink 10 and the cooling block 20 and forms a heat flow path therebetween; a cooling head 30, which is cooled by an external electric cooling device (not shown); and a differential heat flow detectors (thermocouple terminals) 3 and 5 which output as a heat-flow-difference signal a temperature difference between the measuring sample and the reference material.

Note that the exterior of the heater 12 is covered with a cover (not shown).

The heat sink 10 has a cylindrical shape, and a part thereof above a bottom surface 10d positioned at the center in the axial direction constitutes an upper cylinder 10a, and a part thereof below the bottom surface 10d constitutes a lower cylinder 10b. In the internal space surrounded by the bottom surface 10d and the upper cylinder 10a of the heat sink 10, there are arranged a measuring-sample holder 2 and a reference-material holder 4, on which the measuring material and the reference material are set, respectively. Further, the measuring-sample holder 2 and the reference-material holder 4 are connected to the thermocouple terminals 3 and 5, respectively, by metal wires made of metals which is the same as materials of the thermocouple terminals 3 and 5, respectively. The metal wires are drawn out below the heat sink 10, and each of the metal wires is connected to an amplifier 61 so as to form a thermocouple for detecting a differential heat. This enables detection of a temperature difference between the measuring sample and the reference material. The detected temperature difference is recorded as the heat-flow-difference signal. Meanwhile, a thermocouple is drawn out from the thermocouple terminal 3 and is connected to an amplifier 62 so that a temperature of the measuring sample is recorded.

Further, a control thermocouple 18 is attached to the inner surface of the lower cylinder 10b of the heat sink 10, to thereby measure the temperature of the heat sink 10. The output of the control thermocouple 18 is calculated by a proportional-integral-derivative (PID) calculation section 71 including a well-known PID control circuit, and the calculated result is output to a heater drive (driving circuit) 72, to thereby enable control of the temperature of the heater 12.

A lid 11 is detachably mounted on the upper end of the upper cylinder 10a of the heat sink 10 so that the interior of the heat sink 10 is shielded from the external air.

In view of thermal resistance and narrowing of temperature distribution, the heat sink 10 is made of, for example, pure Ag as a material having high thermal conductivity. Therefore, the heat sink 10 has heat capacity large enough with respect to thermal change of the sample.

The cooling block 20 exhibits a substantially rectangular parallelepiped shape in plan view. A cylindrical protruding portion 20p protrudes upward from the center of the cooling block 20, and a part on the outside of the protruding portion 20p constitutes a flat surface, and extends orthogonally downward from the edge of the flat surface to form a lower wall 20d. Further, an outer peripheral surface 20pw of the protruding portion 20p and the flat surface are connected to each other so as to form a step. Note that, though the outer peripheral surface 20pw corresponds to a "side wall" in claims, the lower wall 20d does not correspond to the "side wall". Further, a round hole 20h opened at the center of the protruding portion 20p and the outer peripheral surface 20pw thereof passes through the cooling block 20. Further, a cavity 20a having a rectangular cross-section is provided along the outer periphery of the cooling block 20 in the inside thereof, the cavity 20a being continuous with a cooling gas introducing pipe 40 and a cooling gas discharging pipe 41 attached to the lower wall 20d of the cooling block 20. Accordingly, by introducing, to the cooling gas introducing pipe 40, the cooling gas obtained by evaporation of liquefied nitrogen, the cooling gas composed of the compressed air, or the like, the cooling block 20 itself may be cooled by the gas. Note that the cavity 20a may have a circular cross-section.

Further, poles 50 are attached to four corners of the lower surface of the cooling block 20, respectively, and the cooling block 20 is mounted on a base 52 though the poles 50.

The cooling block 20 functions as a cooling source for cooling the heat sink 10, and heat capacity of the cooling block 20 is set according to cooling ability thereof, ability of the heater 12, a thermal-resistance value to be described later of the thermal resistor 14, and the like. Further, in view of narrowing of the temperature distribution and reduction in cost, the cooling block 20 is made of Cu, Al, or the like as a material having high thermal-conductivity.

Both ends of the thermal resistor 14 is fixed by brazing to the lower end surface of the lower cylinder 10b of the heat sink 10 and an upper end surface 20c of the protruding portion 20p of the cooling block 20, respectively. The thermal resistor 14 is constituted by a large number of rectangular plates, which are separated away from each other in the circumferential direction of the lower end surface of the lower cylinder 10b (and an upper end surface 20u of the protruding portion 20p) and are arranged inside the outer peripheral edges of those end surfaces (see FIG. 2). Note that, in the upper end surface 20u of the protruding portion 20p, an annular shield plate 16 may be attached to the portion on the outside of the thermal resistor 14 so as to further prevent heat inflow through an air layer to the cooling head 30.

Further, of the upper end surface 20u, a connected portion 20c with respect to the lower end of the thermal resistor 14 corresponds to a "connected portion with respect to the thermal resistor" in claims.

The thermal-resistance value of the thermal resistor 14 is determined according to the maximum/minimum achieving temperatures of the heat sink 10, following capability with respect to rise and reduction in temperature, and the like. The temperature difference between the heat sink 10 and the cooling block 20 reaches approximately 600° C. at a maximum, and large thermal stress is applied on the thermal resistor 14. Therefore, the thermal resistor 14 and the heat sink 10 (and the cooling block 20) are connected to each other by brazing and the like.

When the heat resistor 14 is made of pure Fe, it is possible to broaden the range between the maximum/minimum achieving temperatures of the heat sink 10 with the following temperature dependence of the thermal conductivity of the pure Fe: compared with other metal, in the pure Fe, the thermal conductivity decreases more in high temperature and increases more in low temperature.

The cooling head 30 has a substantially rectangular parallelepiped external shape, and a circular inner hole 30i passes therethrough at the center thereof. Further, a connected portion 30c with respect to the external electric cooling device (not shown) extends from the side wall of the cooling head 30 so that the cooling head 30 is cooled by the electric cooling device.

Further, the cooling head 30 covers the upper part of the cooling block 20, and the protruding portion 20p is fitted in the inner hole 30i. As a result, the side surface of the inner hole 30i and the outer peripheral surface 20pw of the protruding portion 20p come in contact with each other, and hence heat is conducted between the cooling head 30 and the cooling block 20. Further, heat is also conducted in the portion at which the lower surface of the cooling head 30 and the upper surface of the cooling block 20 are connected to each other.

In this case, in order to facilitate fitting of the protruding portion 20p into the inner hole 30i, a clearance may be appropriately provided between the side surface of the inner hole 30i and the outer peripheral surface 20pw of the protruding portion 20p. In this case, it is more preferred to fill the clearance with thermal-conductive grease or the like. Further, it is preferred, of course, to use the thermal-conductive grease for connecting the lower surface of the cooling head 30 and the upper surface of the cooling block 20.

Note that the cooling head 30 and the cooling block 20 are fixed to each other with screws (not shown) or the like. Further, the outer diameter of the cooling head 30 is larger than the outer diameter of the cooling block 20, and hence the cooling head 30 completely covers the upper surface of the cooling block 20. In this case, it is sufficient that the contact area between the cooling head and the cooling block is set to be an area sufficient for obtaining required cooling ability of the cooling head.

FIG. 2 is a partial enlarged view of a vicinity of the connected portion 20c of the cooling block 20. An upper surface 30u of the cooling head 30 is not positioned above the connected portion 20c, and is positioned below the connected portion 20c. Therefore, the thermal resistor 14 does not directly face the cooling head 30. As a result, it is possible to suppress heat inflow occurring between the thermal resistor 14 and the cooling head 30 through the air layer.

In this context, the "upper surface of the cooling head 30" means a portion positioned on the uppermost side (heat sink 10 side) when the cooling head 30 is attached to the cooling block 20.

In contrast, when the upper surface 30u of the cooling head 30 is positioned above the connected portion 20c (in the case of a cooling head 30x indicated by a dotted line in FIG. 2), the inner surface of the cooling head 30 directly faces (at a facing portion F in FIG. 2) the thermal resistor 14 through the air layer in the vicinity of the connected portion 20c, and heat inflow occurs between the cooling head 30 and the thermal resistor 14.

Note that, as long as the upper surface 30u of the cooling head 30 is not positioned above the connected portion 20c, the upper surface 30u of the cooling head 30 is not necessarily positioned below the connected portion 20c. That is, the upper surface 30u of the cooling head 30 and the connected portion 20c may be flush with each other.

Further, because the protruding portion 20p is fitted into the inner hole 30i of the cooling head 30 and the outer periphery of the protruding portion 20p is positioned on the outside of the connected portion 20c, a gap F is inevitably formed between the side surface of the inner hole 30i and the connected portion 20c in a side view. Therefore, direct contact between the inner surface of the cooling head 30 and the thermal resistor 14 is prevented. Further, heat conduction is performed through the fitting portion between the inner hole 30i of the cooling head 30 and the outer peripheral surface 20pw of the protruding portion 20p. Therefore, compared with the heat conduction through another fitting portion (for example, fitting portion between the lower surface of the cooling head 30 and the upper surface of the cooling block 20), the heat flow path to the thermal resistor 14 may be made shorter. As a result, cooling speed may be increased and cooling efficiency may be improved.

Further, the inner surface of the cooling head 30 comes in contact with the protruding portion 20p so as to surround the protruding portion 20p. Therefore, heat conduction loss between the cooling head 30 and the cooling block 20 is small, and hence it is possible to enhance cooling efficiency. In particular, when the gap F is reduced (within a finite size other than zero), the heat flow path extending from the cooling head 30 via the cooling block 20 to the thermal resistor 14 is made shorter, and hence the cooling efficiency is improved.

Figure 3:
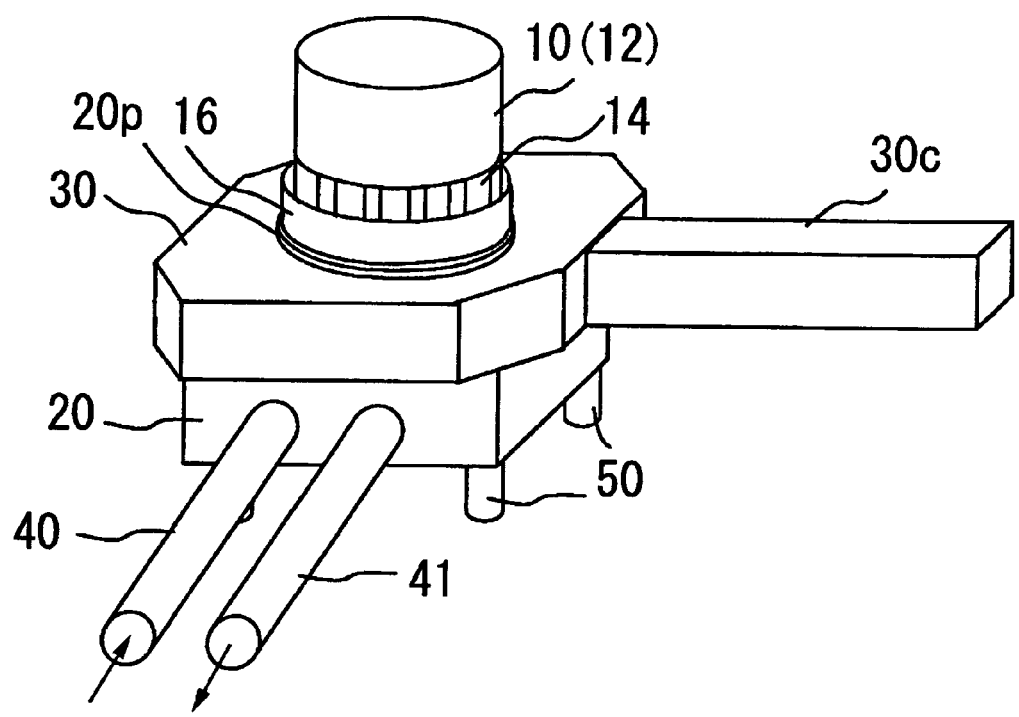
FIG. 3 is a perspective view illustrating a structure of the differential scanning calorimeter.

FIG. 3 is a perspective view illustrating a structure of the differential scanning calorimeter 1. As illustrated in FIG. 3, from the inner hole of the cooling head 30 covering the cooling block 20 from there above, the tip end of the protruding portion 20p of the cooling block 20 is exposed outside, and the thermal resistor 14 is provided upright from the upper surface of the protruding portion 20p. Note that corner portions of the side wall of the cooling head 30 are chamfered. Further, FIG. 3 illustrates the case in which a shield plate 16 is attached.

FIG. 4 is a sectional view illustrating a structure of a differential scanning calorimeter 1B according to a second embodiment of the present invention. Note that, in FIG. 4, description of components and portions the same as those in the differential scanning calorimeter 1 according to the first embodiment is omitted by appropriately omitting illustration or being denoted by the same reference symbols as those in the first embodiment.

In the second embodiment, a cylindrical protruding portion 21p which is the same as that in the first embodiment protrudes upward from a cooling block 21, and constitutes a flat surface on the outside of the protruding portion 21p. Further, an outer peripheral ring 21r is provided upright from the flat surface along the outer peripheral edge of the cooling block 21. The outer peripheral ring 21r surrounds the protruding portion 21p from the outside thereof with a groove 21g therebetween. The outer periphery of the protruding portion 21p, the flat surface of the cooling block 21, and the inner periphery of the outer peripheral ring 21r section the groove 21g.

Meanwhile, the outer diameter of the cooling head 31 is substantially the same as that of the outer periphery of the groove 21g. When the cooling block 21 is covered with the cooling head 31 from above, the cooling head 31 is tightly fitted into the groove 21g while an outer peripheral surface 21pw (corresponding to a "side wall" in claims) of the protruding portion 21p is fitted in the inner hole 31i of the cooling head 31.

Note that, similarly to the first embodiment, the lower end of the thermal resistor 14 is connected to an upper end surface 21u of the cooling block 21, to thereby constitutes a connected portion 21c (corresponding to a "connected portion connected to the thermal resistor" in claims).

Also in the second embodiment, an upper surface 31u of the cooling head 31 is positioned below the connected portion 21c. Therefore, the thermal resistor 14 does not directly face the cooling head 31, and hence it is possible to suppress heat inflow between the thermal resistor 14 and the cooling head 31 through the air layer.

Further, the protruding portion 21p is fitted in the inner hole 31i of the cooling head 31, and the outer periphery of the protruding portion 21p is positioned on the outside of the connected portion 21c. Therefore, in a side view, a gap (same as the gap F) is inevitably formed between the side surface of the inner hole 31i and the connected portion 21c. Therefore, direct contact between the inner surface of the cooling head 31 and the thermal resistor 14 is prevented.

Further, in the second embodiment, the cooling head 31 is housed in the groove 21g. Therefore, heat conduction is performed also through the contact portion between the outer periphery of the cooling head 31 and the inner surface of the outer peripheral ring 21r, and hence the heat conduction loss between the cooling head 31 and the cooling block 21 is further reduced than that in the first embodiment. As a result, cooling efficiency may be further enhanced.

Figure 5:
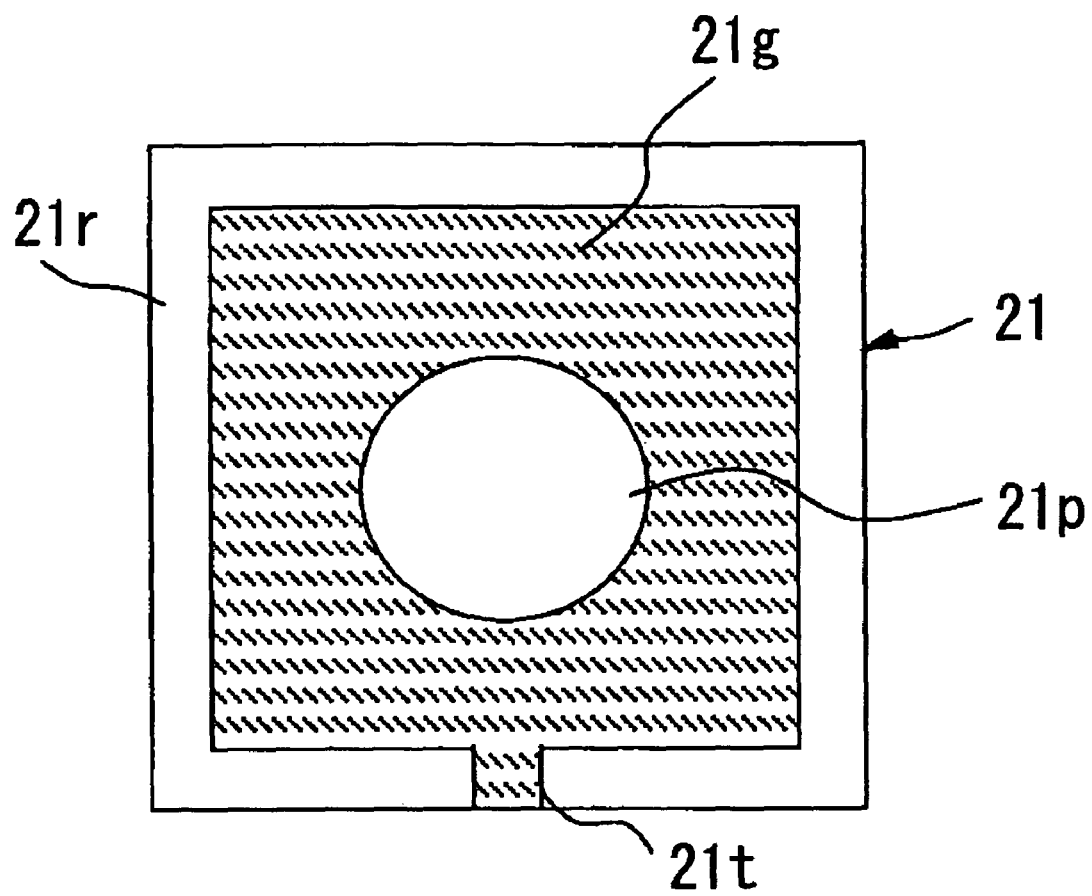
FIG. 5 is a top view of the differential scanning calorimeter according to the second embodiment.

FIG. 5 is a top view of the differential scanning calorimeter 1B according to the second embodiment. As illustrated in FIG. 5, the rectangular outer peripheral ring 21r extends upright from the peripheral edge of the rectangular cooling block 21, to thereby constitute the outer peripheral wall of the groove 21g. Meanwhile, the inner peripheral wall of the groove 21g is formed of the cylindrical protruding portion 21p. As described above, regarding an "annular groove" in claims, the inner periphery and the outer periphery of the groove may have different shapes from each other. Further, the shape of the groove is not limited to the circular shape, and may be various shapes such as the rectangular shape. Further, the outer peripheral ring 21r may extend upright from a predetermined position inside the peripheral edge of the cooling block 21.

Note that a cutout 21t is formed in a part of the outer peripheral ring 21r so that the outer peripheral ring 21r does not interfere with a connected portion 31c extending laterally from the cooling head 31.

Figure 6:
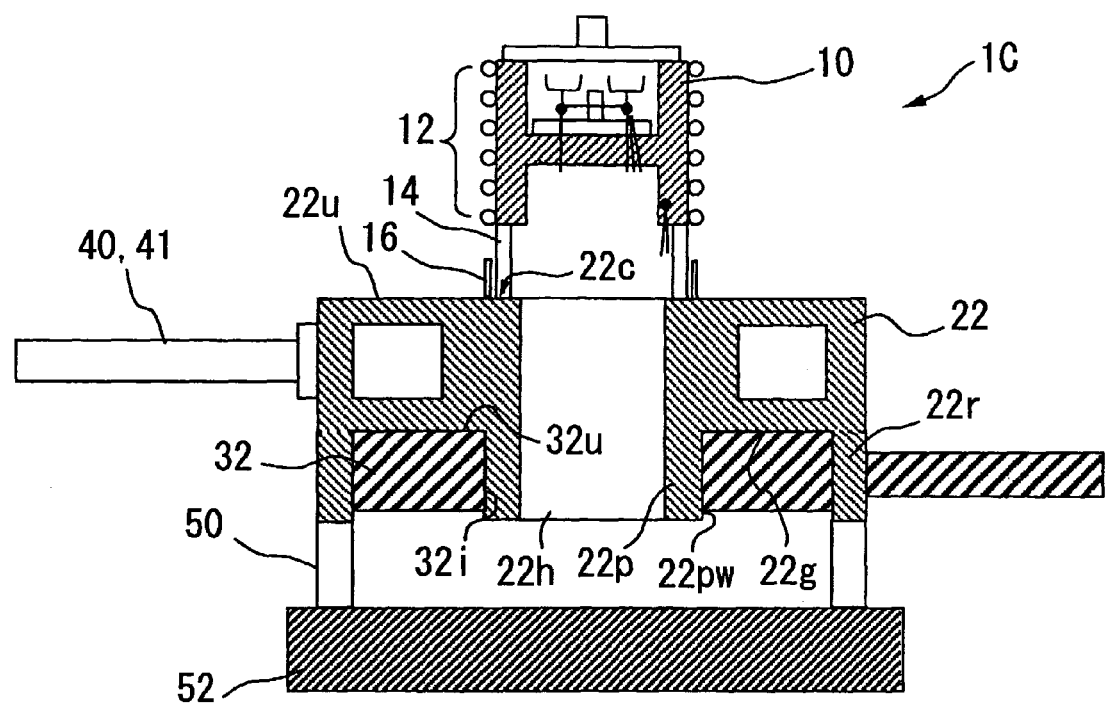
FIG. 6 is a sectional view illustrating a structure of a differential scanning calorimeter according to a third embodiment of the present invention.

FIG. 6 is a sectional view illustrating a structure of a differential scanning calorimeter 1C according to a third embodiment of the present invention. Note that, in FIG. 6, description of components and portions the same as those in the differential scanning calorimeter 1 according to the first embodiment is omitted by appropriately omitting illustration or being denoted by the same reference symbols as those in the first embodiment.

In the third embodiment, a cooling block 22 has a structure in which the same cooling block as the cooling block 21 in the second embodiment is arranged upside down. That is, a cylindrical protruding portion 22p protrudes downward from the cooling block 22, a flat surface is formed on the outside of the protruding portion 22p, and an outer peripheral ring 22r extends downward from the flat surface along the outer peripheral edge of the cooling block 22. The outer peripheral ring 22r surrounds the protruding portion 22p from the outside thereof with a groove 22g therebetween. The outer periphery of the protruding portion 22p, the flat surface of the cooling block 22, and the inner periphery of the outer peripheral ring 22r section the groove 22g.

Meanwhile, the outer diameter of the cooling head 32 is substantially the same as that of the outer periphery of the groove 22g. When the cooling block 22 is covered with the cooling head 32 from below, the cooling head 32 is tightly fitted into the groove 22g while an outer peripheral surface 22pw (corresponding to a "side wall" in claims) of the protruding portion 22p is fitted in the inner hole 32i of the cooling head 32.

Note that the poles 50 are attached to the lower end edge of the outer peripheral ring 22r.

In the third embodiment, the lower end of the thermal resistor 14 is connected to an upper surface 22u of the cooling block 22 along the outer periphery of a round hole 22h, to thereby constitute a connected portion 22c (corresponding to a "connected portion connected to the thermal resistor" in claims). Further, the connected portion 22c is positioned inside the outer periphery of the protruding portion 22p.

Further, the cooling head 32 is positioned below the cooling block 22, and hence an upper surface 32u of the cooling head 32 is positioned below the connected portion 22c. Therefore, the thermal resistor 14 does not directly face the cooling head 32, and hence it is possible to suppress heat inflow through the air layer between the thermal resistor 14 and the cooling head 32.

Further, the protruding portion 22p is fitted into an inner hole 32i of the cooling head 32, and the outer periphery of the protruding portion 22p is positioned on the outside of the connected portion 22c. Therefore, in a side view, a gap (same as the gap F) is inevitably formed between the side surface of the inner hole 32i and the connected portion 22c. Therefore, direct contact between the inner surface of the cooling head 32 and the thermal resistor 14 is prevented.

Further, in the third embodiment, the cooling head 32 is housed in the groove 22g. Therefore, heat conduction is performed also through the contact portion between the outer periphery of the cooling head 32 and the inner surface of the outer peripheral ring 22r, and hence the heat conduction loss between the cooling head 32 and the cooling block 22 is further reduced than that in the first embodiment. As a result, cooling efficiency may be further enhanced.

Figure 7:
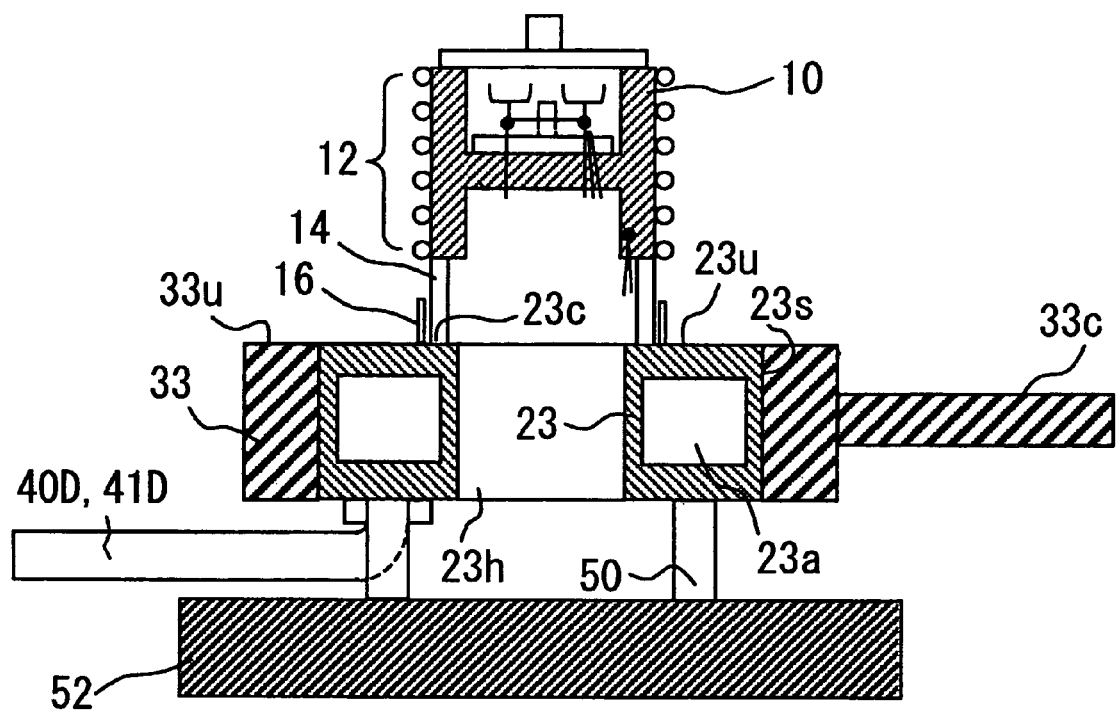
FIG. 7 is a sectional view illustrating a structure of a differential scanning calorimeter according to a fourth embodiment of the present invention.

FIG. 7 is a sectional view illustrating a structure of a differential scanning calorimeter 1D according to a fourth embodiment of the present invention. Note that, in FIG. 7, description of components and portions the same as those in the differential scanning calorimeter 1 according to the first embodiment is omitted by appropriately omitting illustration or being denoted by the same reference symbols as those in the first embodiment.

In the fourth embodiment, a cooling block 23 has a substantially rectangular parallelepiped shape without the protruding portion, and a round hole 23h passes through the cooling block 23 at the center thereof. Further, a cavity 23a having a rectangular cross-section is provided along the outer periphery of the cooling block 23 in the inside thereof, the cavity 23a being continuous with a cooling gas introducing pipe 40D and a cooling gas discharging pipe 41D attached to the lower surface of the cooling block 23. Note that the pipes 40D and 41D are bent from the lower surface of the cooling block 23 at 90 degrees so as to extend laterally.

Meanwhile, the cooling head 33 has a substantially rectangular parallelepiped external shape, and a rectangular inner hole 31i having an inner diameter slightly larger than the outer diameter of the cooling block 23 passes therethrough at the center thereof. Further, a connected portion 33c with respect to the external electric cooling device (not shown) extends from the side wall of the cooling head 33 so that the cooling head 33 is cooled by the electric cooling device.

Further, when the exterior of the cooling block 23 is covered with the cooling head 33, the cooling head 33 is tightly fitted to the cooling block 23 while a side wall 23s (corresponding to a "side wall" in claims) of the cooling block 23 is fitted in the rectangular inner hole 33i of the cooling head 33. In this case, the cooling head 33 and the cooling block 23 are attached to each other so that an upper surface 33u of the cooling head 33 and an upper surface 23u of the cooling block 23 are flush with each other.

Further, in the fourth embodiment, the lower end of the thermal resistor 14 is connected to the upper surface 23u of the cooling block 23 along the outer periphery of the round hole 23h, to thereby constitute a connected portion 23c (corresponding to a "connected portion connected to the thermal resistor" in claims).

As described above, the upper surface 33u of the cooling head 33 is not positioned above the connected portion 23c. Therefore, the thermal resistor 14 does not directly face the cooling head 33, and hence it is possible to suppress heat inflow between the thermal resistor 14 and the cooling head 33 through the air layer.

Further, the side wall 23s of the cooling block 23 is fitted in the inner hole 33i of the cooling head 33, and the side wall 23s is positioned on the outside of the connected portion 23c. Therefore, in a side view, a gap (same as the gap F) is inevitably formed between the side surface of the inner hole 33i and the connected portion 23c. Therefore, direct contact between the inner surface of the cooling head 33 and the thermal resistor 14 is prevented.

Note that, though the upper surface 33u of the cooling head 33 and the upper surface 23u of the cooling block 23 are flush with each other in the fourth embodiment, the upper surface 33u may be attached lower than the upper surface 23u.

It goes without saying that the present invention is not limited to the above-mentioned embodiments and includes various modifications and equivalents within the idea and the scope of the present invention.

Further, the external cooling device for cooling the cooling head is not limited to the electric cooling device, and a gas cooling device that vaporizes liquefied nitrogen and the like or supplies the compressed air may be used. In the latter case, a flow path through which the gas from the gas cooling device flows in and out may be provided in the cooling head.

What is claimed is:

1. A differential scanning calorimeter, comprising:
   a heat sink, which stores a measuring sample and a reference material;
   a heater, which heats the heat sink;
   a cooling block, which is separated away from the heat sink, and is positioned below the heat sink;
   a thermal resistor, which is connected between the heat sink and the cooling block, and forms a heat flow path therebetween;
   a cooling head, which is provided with an inner hole for allowing the cooling head to be detachably fitted to the cooling block, and is cooled by an external cooling device; and
   differential heat flow detectors, which output a temperature difference between the measuring sample and the reference material as a heat-flow-difference signal, wherein:
   the cooling block has a side wall, which is formed on an outside of a connected portion connected to the thermal resistor, and is fitted to the inner hole; and
   the cooling head is arranged so that an upper surface thereof is positioned flush with or below the connected portion.

2. A differential scanning calorimeter according to claim 1, wherein the side wall comprises an outer peripheral surface of a protruding portion protruding upward or downward from the cooling block.

3. A differential scanning calorimeter according to claim 2, wherein:
   in one of an upper surface and a lower surface of the cooling block, an annular groove is formed, the annular groove being sectioned by the protruding portion and an outer peripheral ring surrounding the protruding portion from an outside thereof with the annular groove therebetween; and
   the cooling head is housed in the annular groove and the protruding portion is fitted into the inner hole.

* * * * *